US010861607B2

(12) United States Patent
Ahrens et al.

(10) Patent No.: US 10,861,607 B2
(45) Date of Patent: Dec. 8, 2020

(54) METHOD FOR SETTING UP A FLUID PROCESSING MEDICAL APPARATUS (71) Applicant: B. BRAUN AVITUM AG, Melsungen (DE)

(72) Inventors: Jörn Ahrens, Baunatal (DE); Botond Tényi, Budakalász (HU)

(73) Assignee: B. BRAUN AVITUM AG, Melsungen (DE)

( * ) Notice: Subject to any disclaimer, the term of this patent is extended or adjusted under 35 U.S.C. 154(b) by 248 days.

(21) Appl. No.: 15/426,480

(22) Filed: Feb. 7, 2017

(65) Prior Publication Data
US 2017/0228509 A1 Aug. 10, 2017

(30) Foreign Application Priority Data

Feb. 8, 2016 (EP) .................................. 16154702

(51) Int. Cl.
*A61M 1/10* (2006.01)
*G16H 70/40* (2018.01)
*G16H 40/63* (2018.01)
*G16H 40/20* (2018.01)
*G16H 20/17* (2018.01)
*A61M 1/14* (2006.01)
*A61M 1/36* (2006.01)
(Continued)

(52) U.S. Cl.
CPC .......... *G16H 70/40* (2018.01); *A61M 1/1039* (2014.02); *A61M 1/1081* (2013.01); *A61M 1/1086* (2013.01); *A61M 1/14* (2013.01); *A61M 1/3621* (2013.01); *G06K 7/12* (2013.01); *G06K 7/1413* (2013.01); *G16H 20/17* (2018.01); *G16H 40/20* (2018.01); *G16H 40/63* (2018.01); *A61M 2205/12* (2013.01); *A61M 2205/18* (2013.01); *A61M 2205/505* (2013.01); *A61M 2205/6018* (2013.01); *A61M 2205/6072* (2013.01); *A61M 2205/6081* (2013.01)

(58) Field of Classification Search
CPC .... A61M 1/1039; A61M 1/1081; G16H 40/63
USPC .......................................................... 705/2
See application file for complete search history.

(56) References Cited

U.S. PATENT DOCUMENTS 8,747,662 B2 6/2014 Delmage et al.
2005/0070837 A1* 3/2005 Ferrarini ................. A61M 1/14
604/5.01

(Continued)

FOREIGN PATENT DOCUMENTS

EP 1 668 556 6/2006
WO WO2005031628 4/2005
WO WO 2008/129344 10/2008

OTHER PUBLICATIONS

European Search Report for EP 16154702.1 dated Jun. 21, 2016.

*Primary Examiner* — Reginald R Reyes (57) ABSTRACT

A method for setting-up a fluid processing medical apparatus, the method includes: a) positioning a disposable component intended to be used for therapy with the fluid processing medical apparatus relative to a reader unit by a user; b) reading component related information provided on the disposable component by the reader unit; c) matching the read component related information with component related data stored in a database; and d) providing a selection of suitable therapies for the disposable component to the user based on the matching.

14 Claims, 4 Drawing Sheets (51) Int. Cl.
   *G06K 7/12*   (2006.01)
   *G06K 7/14*   (2006.01)

(56) References Cited

U.S. PATENT DOCUMENTS

| | | | |
|---|---|---|---|
| 2008/0176210 A1* | 7/2008 | Moll | G16H 40/63 |
| | | | 435/2 |
| 2012/0138533 A1 | 6/2012 | Curtis et al. | |
| 2015/0134547 A1* | 5/2015 | Oikonomidis | G06F 16/9554 |
| | | | 705/306 |
| 2017/0290970 A1* | 10/2017 | Friederichs | A61M 1/1664 |

* cited by examiner

METHOD FOR SETTING UP A FLUID PROCESSING MEDICAL APPARATUS

CROSS REFERENCE TO RELATED APPLICATIONS

This application claims priority to German Application EP 16154702.1 filed Feb. 8, 2016, the contents of such application being incorporated by reference herein.

FIELD OF THE INVENTION

The invention concerns a method for setting up a fluid processing medical apparatus, in particular for extracorporeal blood treatment, and a fluid processing medical apparatus.

BACKGROUND OF THE INVENTION

Modern CRRT (Continuous renal replacement therapy) devices contain a reader unit that allows to read information provided on a disposable component into the device. Such information can be used to protect against use of obsolete disposables and also amplify usability in that not all information has to be entered manually. Information on type of disposable can be used to ensure that scheduled therapy is feasible to be performed with disposable and not a wrong application is performed. Usually, a user first selects a therapy he intends to perform. After selecting a therapy or after a change of a disposable component a new disposable component intended to be used is scanned by use of a reader. If the selection is not meeting the information of reader data content, known devices provide an alarm and display that a wrong disposable has been scanned.

DESCRIPTION OF THE RELATED ART

WO 2008/129344 A1 discloses a similar method for setting up a fluid treatment apparatus using a single, and always accessible, reader of information relating to replaceable components, which are to be mounted on the apparatus to perform the fluid treatment. It also discloses a fluid treatment apparatus having an always accessible reader. The reader can be relied on to enter information other that those relating to the replaceable components, such as commands for the apparatus, patients' related information, etc.

Disadvantages and shortcomings of current state of the art solutions are, for example, that a user first has to select the final therapy in all details on a first screen. The user in this case is usually confronted with a high number of different therapies and combinations of therapies, he has to choose.

SUMMARY OF THE INVENTION

It is an object of the invention to provide an alternative solution for known prior art methods and especially to improve the usability for the user and to make setting up of the medical apparatus easier.

According to aspects of the invention this object is solved by a method for setting up a fluid processing medical apparatus, in particular for extracorporeal blood treatment, the method comprising the following steps:

a) positioning a disposable component intended to be used for therapy with the fluid processing medical apparatus relative to a reader unit by a user, b) reading component related information provided on the disposable component by the reader unit, c) matching the read component related information with component related data stored in a database, and d) providing a selection of suitable therapies for the disposable component to the user based on the matching of step c).

It is an advantage of the invention that there is provided a simple way of setting up a fluid processing medical apparatus and reaching therapy start by the user. Within the present invention different ways are feasible to support ease of use and avoid mistakes inside preparation probes. One could say that one concept of the invention is not to provide an error message, when a disposable component is read and is not fitting into a suitable selection—as in the prior art—but to only display a list of possible therapies with regard to the read disposable component for a selection by the user after reading the possibilities offered by the system. Accordingly, the invention does not require an alarm function for a not suitable therapy selection and allows the user only to see a small range of any therapies at a first instance. A long and complete list of all therapies would otherwise require a wide overview of all possibilities. Therefore, the invention allows a quick and easy way of setting the fluid processing medical apparatus by a pre-selection of only suitable therapies (with regard to the disposable component read) for user to be selected.

According to aspects of the invention, a user first has to select and/or to take a disposable component or kit of disposable components that he believes to be adequate or suitable or intended for a scheduled therapy. The disposable component chosen by the user is then positioned in an adequate manner relative to the reader unit and the component related information provided thereon is read with reader unit. Positioning can be performed manually by the user or a third person, like medical staff, or can be performed automatically.

The information provided on the concerning disposable component can be a disposable component ID and/or contain information on certain properties or features of the concerning disposable device. The component ID as well as the information can be provided e.g. in form of a bar code, color code or any similar optical code printed or otherwise provided on the disposable device, and/or in form of data contained in a readable data storage unit being part of the disposable device, as an RFID-device, a microchip, a mechanical key, etc. The information can be—as already stated—a simple ID for identifying the component and/or additionally or alternatively contain data concerning type, shelf life, manufacturer, production details, production data, date of expiry, therapies performable with the concerning disposable component, therapy data or other component parameters or system parameters. Therefore, step c) has to be understood such, that the component related data may already be stored on a data store provided with the disposable component and/or may be contained in a database that is separate from the disposable component but accessible by using the component ID. One can say that according to aspects of the invention an information on the disposable component and/or the type of the disposable component can be used to ensure that a scheduled therapy is feasible to be performed with the correct and suitable disposable and that no wrong or incorrect or incomplete application is performed. Besides that, within the invention the system can use certain information on the disposable component (e.g. filter size, priming volume, etc.) to optimize system processes or therapy processes.

According to aspects of the invention, a selection of suitable therapies for the concerning disposable component is provided depending from the component related information and/or from the component related data. In this regard, steps c) and d) of the method of the invention are performed automatically, for example by a processor unit or a control unit each being part of the fluid processing medical apparatus. The selection provided is therefore limited to therapies that can be performed with the concerning disposable component, that has been selected by the user and read by the reader unit. This is an essential difference and advantage with regard to the prior art, because the user has to deal with a limited number of possibilities for therapy, only. It makes the use and especially the setting up of the fluid processing medical apparatus and of the therapy to be performed much easier for the user, who in many cases may not be a medical expert, but inexperienced staff or users (e.g. home dialysis), which are not frequently using the device.

Examples for therapies provided in the selection and to be performed with the fluid processing medical apparatus are at least one of a therapy type (e.g. Slow Continuous Ultrafiltration (SCUF), Continuous Veno-Venous Hemofiltration (CVVH), Continuous Veno-Venous Hemodialysis (CVVHD), Continuous Veno-Venous Hemodiafiltration (CVVHDF), Therapeutic Plasma Exchange (TPE), Hemoperfusion (HP), Cascade Filtration (CF), Plasma Adsorption (PA), Low Blood Volume (LBV), etc.), a dilution type (e.g. Pre Dilution, Post Dilution, Pre-Post Dilution, Post-Post Dilution, etc.) and an anticoagulation type (e.g. none, Heparin, Citrate, etc.).

According to one embodiment of the invention the component related information provided on the disposable component may comprise a date of expiration and the step c) may only be performed, if the disposable component has not expired. In case of an expired disposable component, a user may be prompted (acoustical or optical warning) to repeat step a) with another (not yet expired) disposable component According to one embodiment of the invention, the method further comprises a step e) performed after step d) of selecting one of the suitable therapies of the provided selection for therapy. Such a selection is performed by the user. He can enter his decision manually or by just ticking one of the provided therapies for example on a touch screen.

The method may further comprise a step of returning to step a) and/or step b) in case the selection provided in step d) is not meeting the requirements of the user. Such an additional step is useful in a case, where the user unintentionally has chosen a wrong disposable unit, which is not adequate for the therapy to be applied to the user. Another case is, when the expiry date of the chosen disposable component has expired and the component must not be used any more. The user then can choose another disposable component that he thinks is suitable and perform the method from the beginning. The method may further comprise a step of coupling the disposable component with the fluid processing medical apparatus for therapy and/or performing therapy.

According to one embodiment, the reader unit for reading information provided on a disposable component intended to be used for therapy is comprised by the fluid processing medical apparatus. In this manner a very compact apparatus for performing the method of the invention can be provided. The reader may be any optical reader, such as a bar code reader, a color code reader, a QR code reader or a reader of any optically detectable shape and/or pattern, or a radio-frequency reader, for example an RFID reader, or a magnetic reader or any other equivalent reader adapted to detect the information provided on the disposable component when the latter and the reader unit are approached one another (in contact or in proximity).

According to a further embodiment, the selection of possible therapies in step d) is shown on a display device, the display device preferably forming part of the fluid processing medical apparatus. Preferably, the display unit is a monitor or touch screen.

The database may comprise a concordance table or concordance matrix assigning the component related information, in particular a disposable component-ID, to component related data on at least one of the group of identity of the disposable component, identity of a series of identical disposable components, manufacturer, production details, production data, date of expiry, therapies performable with the concerning disposable component, therapy data.

In a case of a change of a disposable component during a running therapy, according to aspects of the invention information provided on the new disposable component the user intends to use can be read. The system reads in only the proper new component relevant to the current therapy. If it is not adequate for use due to other reasons, e.g. because of expiry, the system does not accept the component. In this latter case the system may further issue a message or warning to the user that the disposable cannot be used. Further, the user may be invited or the system is waiting for scanning another adequate or right component.

According to a further embodiment, if no machine readable information is available with the disposable component or if such information is disrupted, such information may be entered by the user manually. In such a case, the system may provide a message to the user inviting him to manually enter such information.

Another aspect of the invention relates to a fluid processing medical apparatus comprising a controller configured to control operation of the fluid processing medical apparatus, a reader unit configured to read component related information provided on a disposable component to be used in the fluid processing medical apparatus and being positioned relative to the reader unit by a user, a display unit configured to display control and operation information of the fluid processing medical apparatus. The controller is configured to a) match component related information read by the reader unit with component related data stored in a database within the fluid processing medical apparatus or a database connected to the fluid processing medical apparatus via a network, and b) provide a selection of suitable therapies for the disposable component to the user based on the matching of step a) with the display unit.

According to one embodiment the display unit may be a touch screen allowing a user to select a suitable therapy displayed on the display unit, wherein the controller may be operate components of the fluid processing medical apparatus, in particular one or more peristaltic pumps and/or syringes, in accordance with the selected therapy.

According to one embodiment the controller may be configured to allow the user to read component related information provided on another disposable component by the reader unit in case the selection provided in step b) is not meeting the requirements of the user.

According to one embodiment, upon selection of a therapy, the controller may be configured to display on the display unit to the user one or more steps of correctly installing the disposable component at the fluid processing medical apparatus.

According to one embodiment the fluid processing medical apparatus may comprise one or more sensors configured to detect a correct installation of the disposable component, wherein the controller is configured to start the selected therapy only after correct installation of the disposable component detected by the one or more sensors.

According to one embodiment the database may comprise a concordance table or concordance matrix assigning the component related information, in particular a disposable component-ID, to component related data on at least one of the group of identity of the disposable component, identity of a series of identical disposable components, manufacturer, production details, production data, expiration date, therapies performable with the concerning disposable component, and/or therapy data.

According to one embodiment the controller may be configured to deactivate the reader unit upon selection of the therapy type.

It is within the scope of invention to combine the aforementioned embodiments in any possible manner.

By the invention inter alia the following advantages may be achieved:
  avoiding of misunderstandings for a user in future, if similar disposable components only differ in detail.
  a selection of a disposable component by the user results in providing a simple list of possible feasible therapies.

Especially and expressed with other words, it is the invention's aim or target to provide the user a more simple way of reaching therapy start. Different ways are feasible within the invention to support ease of use and to avoid mistakes inside the preparation process. Beside the user interface itself, according to aspects of the invention further inputs are feasible to enhance usability process in a fast and secure way. According to aspects of the invention a first general information on the method and actions to be taken by the user may be shown on a first start screen. The user can very easily select the therapy to be applied from a feasible set of therapy selections. It is a big advantage that on the screen there are only provided therapies and/or therapy modalities that can be performed with the disposable component or the type of disposable component as read by the reading unit. This allows a user friendly start of a therapy. Different from known methods for setting-up a fluid processing medical apparatus, the user can select from a limited number of possible therapies instead of being forced to handle a huge amount of therapies, type of combinations and options that can be performed by the concerning fluid processing medical apparatus. This makes the method of the invention much easier to handle for the user.

Further, after reading the information provided on the disposable component a number of options are indicated to the user that are feasible with the disposable component the user had selected and that has been read by the reader unit. With other words, the invention provides a possibility to give an overview of all feasible options and also all possible changes during a therapy in relation to the read disposable component. Such options and changes are clearly visible for the user and shown on the display unit. In this manner it is ensured that all required expectations are feasible.

The invention especially allows to perform any therapy and/or any therapy-mode that can be performed with the concerning disposable component and also allows very easy switching between different therapy modes. Changing between different feasible therapies and modalities of therapy can be performed during a running therapy due to a fully read, realized and pre-connected fluid processing medical apparatus.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
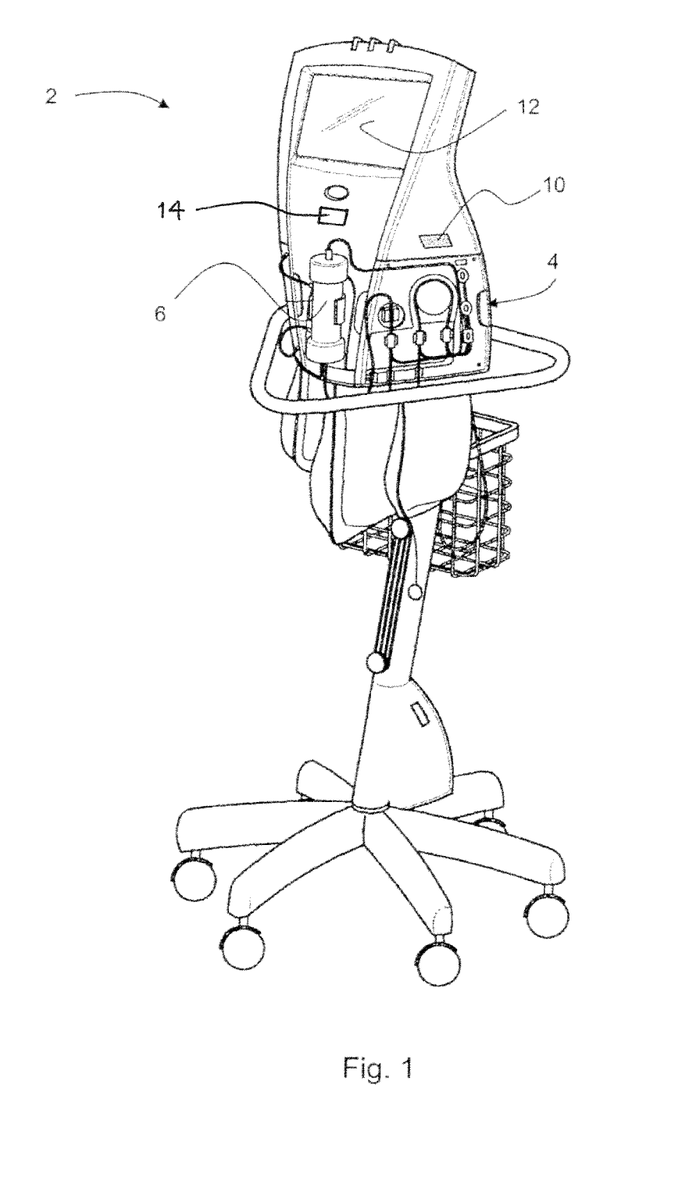
FIG. 1 shows a perspective view of a fluid processing medical apparatus including an installed disposable kit according to aspects of the invention.

FIG. 1 shows fluid processing medical apparatus 2 to be used for continuous renal replacement therapy, such as a dialysis apparatus. A disposable kit or set 4 is attached to the fluid processing medical apparatus 2. Such disposable kit 4, which is shown in detail in FIG. 2, includes a preconfigured arrangement of tubing sets mounted on the panels and configured for easy installation and replacement on the housing of the fluid processing medical apparatus 2. The tubing kits on each of the different panels are configured and formed to readily engage one or more of the peristaltic pumps and for being connected to or disconnected from a filter cartridge 6 that is also installed at the fluid processing medical apparatus 2, fluid supply bags, waste bags, etc. An example configuration of the disposable kit 4 and its coupling to the fluid processing medical apparatus 2 is disclosed in more detail in U.S. Pat. No. 8,747,662 B2, which description is incorporated by reference.

Figure 2:
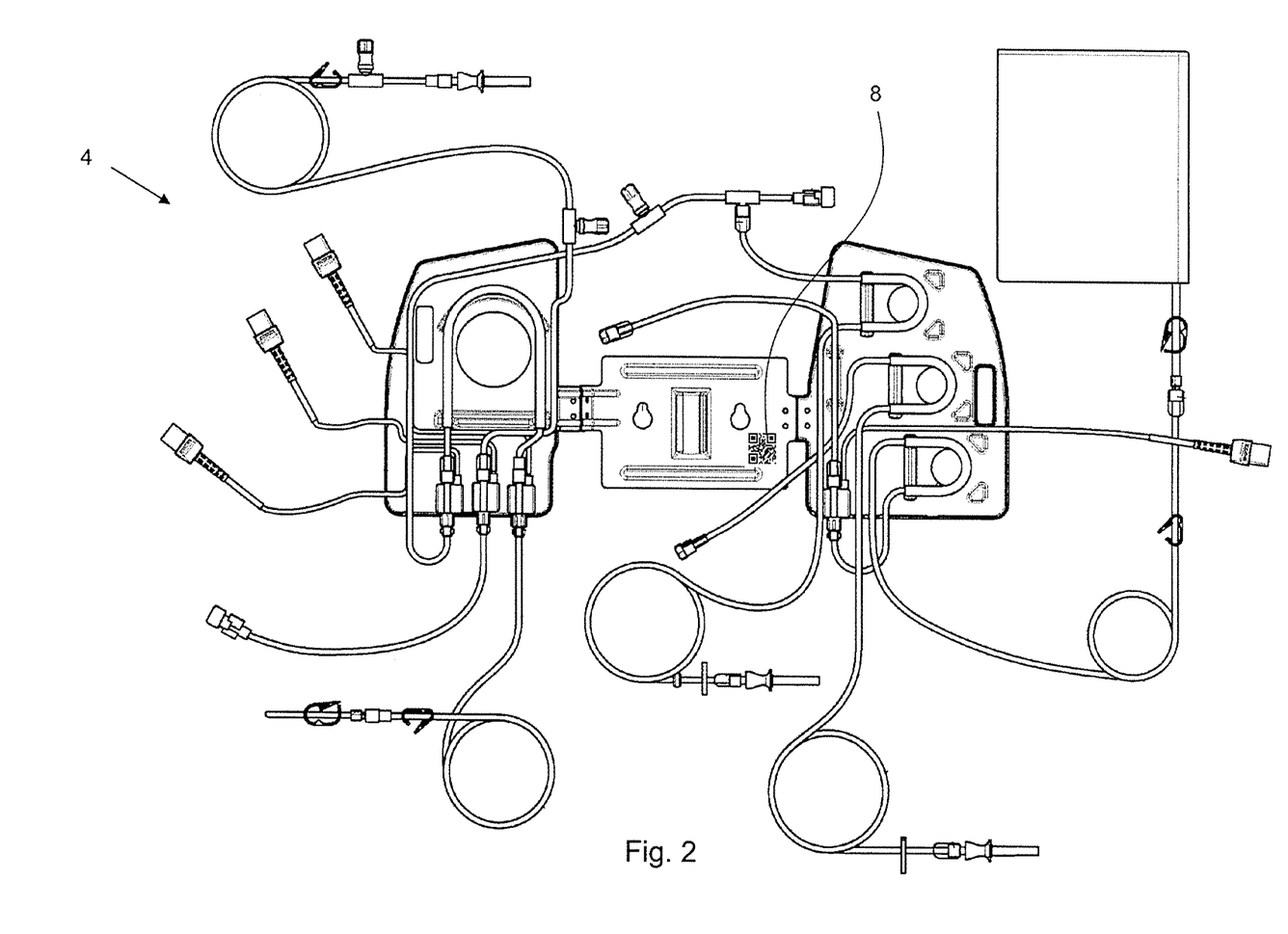
FIG. 2 shows the disposable kit before its installation at the fluid processing medical apparatus.

One or all of the disposable components itself or packagings thereof, i.e. the disposable kit 4, the filter cartridge 6, etc., may be provided with a machine readable information on the component in form of a bar code, QR code, RFID code, etc. As shown in FIG. 2, the disposable kit 4 is provided with a QR code 8 that can be read by a reader unit or scanner 10 provided in the housing of the fluid processing medical apparatus 2. The information contained in the QR code can be read by the reader unit 10 and processed by a control unit or processor unit 14 of the fluid processing medical apparatus 2. The machine readable information may contain at least one of a component type, component ID or LOT number, and an expiration date of the disposable component. Such information may be displayed on a screen 12 of the fluid processing medical apparatus 2. The screen 12 can be implemented as a touch screen so as to allow a user also to enter data or select different therapy options and/or parameters displayed on the screen 12.

Figure 3:
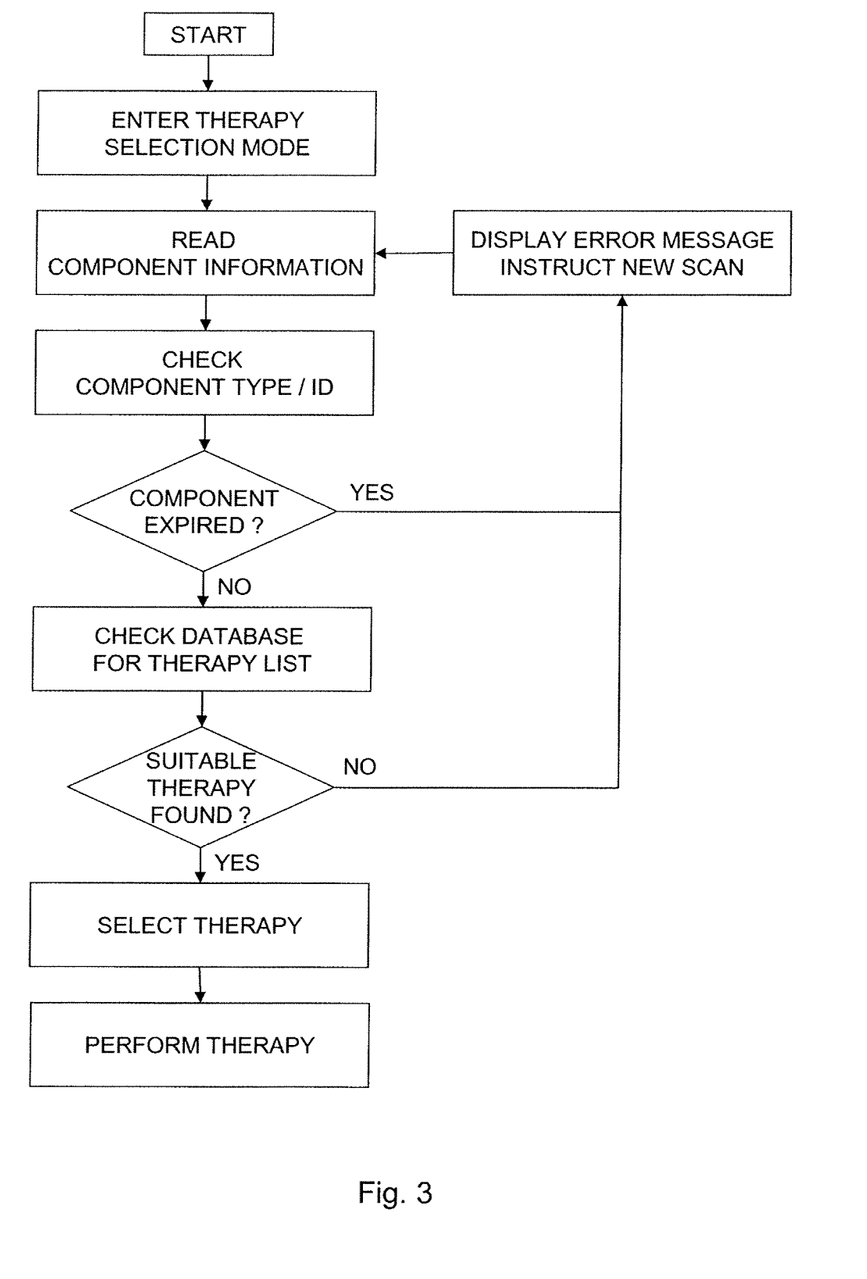
FIG. 3 shows in a schematic illustration a flow diagram of an exemplary process for setting up the fluid processing medical apparatus according to aspects of the invention.

FIG. 3 shows an exemplary flow chart of the method of the invention. In a first step a user starts the apparatus and then enters into a therapy selection mode. Afterwards the user takes a certain disposable component he believes to be suitable for the therapy to be performed. He positions the component relative to a reader unit, here a scanner. The information provided on the disposable component is read/scanned. Based on this read information, in a next step the system checks, whether or not the component is expired. In the case of an expired component, the system gives an alarm and informs the user about this, for example by showing a concerning message on a display device. The system in such case may not allow any further operation, except for reading information of another disposable component to determine, if this other component has been expired, too. The system may repeat these steps until a disposable component is scanned, which according to its information is not expired. As an alternative, the system may alert that the component has been expired, but the user may nevertheless manually enter the therapy selection.

In the case that a non-expired component has been scanned, the system provides a list of suitable and/or possible and/or feasible therapies. This selection of therapies is made dependent from the information provided with the disposable component. This means that the user has to deal only with therapies or sets of therapies that can be performed with the scanned disposable device, which may be a very limited number of possibilities with regard the any therapy that can be performed on the fluid processing medical apparatus. It is therefore much easier for the user to choose and select the correct therapy.

If the user realized that the therapy he intended to perform is not offered in the selection, maybe because the user scanned a wrong or unsuitable disposable component, or if a selection provided by the system after reading a certain disposable component does not meet the users expectation, he may go back to the scanning step and perform an additional scanning of another component. This establishes a kind of fallback position to avoid performance of wrong therapies.

In case the user wishes to perform one of possibilities offered in the selection, he has to install the scanned concerning disposable component in the apparatus and to select the concerning possibility he wishes to perform. The system then may check, if the correct component is indeed installed and will perform the selected therapy or steps.

Figure 4:
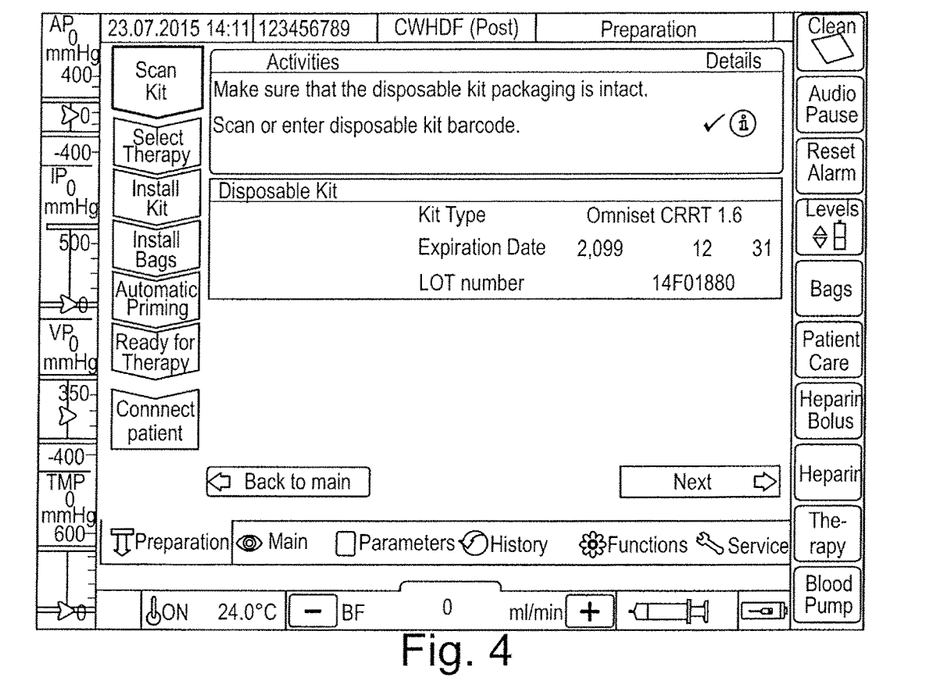
FIG. 4 shows a screen shot of a user interface display in a first state of the method of the invention.
Figure 5:
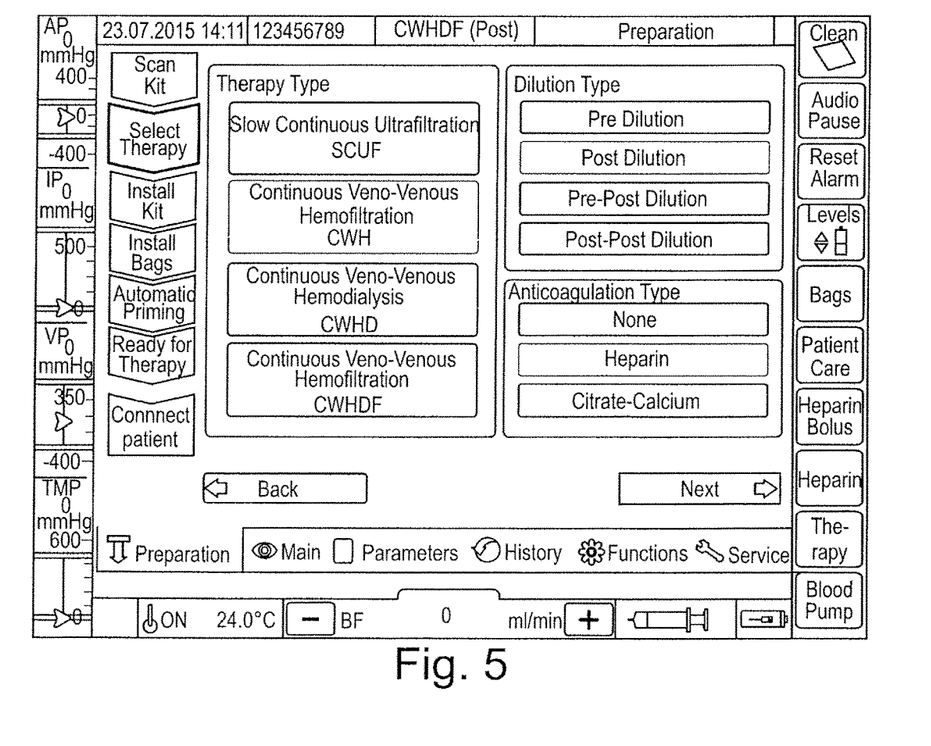
FIG. 5 shows a screen shot of a user interface display in a second state of the method of the invention.

FIGS. 4 and 5, respectively, show a screen shot taken from a touch screen of a fluid processing medical apparatus during a first state and a second state of the method of invention. FIG. 4 shows the display at the beginning of the setting up prior to step a). On the left side of the display there is provided a list of steps to be performed by the user during the setting up method. Each step may be highlighted in the concerning state of method to indicate to the user a next action to be taken by him. In FIG. 4 there is highlighted an instruction tab "scan kit", which invites the user to select a certain disposable component and to read the information provided therewith by using the reader unit of the medical apparatus. Further instructions, which are not highlighted at this stage of proceedings, are "select therapy", "install kit", "install bags", "automatic priming", "ready for therapy" and "connect patient". In the middle of the screen there are shown further advices or additional information, here additional information about the disposable component read by the reader, as component ID, expiry date, LOT number, etc.

FIG. 5 shows the screen in a further state of setting up after the system has performed step d) of the method of the invention. On the left of the screen, the next instruction tab "select therapy" is highlighted, while in the middle of the screen the therapies are listed, that were found by the system in the database in relation to the read disposable component information.

The invention claimed is:
1. A method for setting-up a fluid processing medical apparatus, the method comprising the steps of:

a) reading component related information provided on a first disposable component by a reader unit, the component related information including a first date of expiration; and
b) confirming that the first disposable component is unexpired based on the first date of expiration,
wherein, if the first disposable component is confirmed to be unexpired in step b), then the method proceeds with:
c) matching the read component related information with component related data stored in a database;
d) displaying a selection of suitable therapies for the first disposable component to the user based on the matching of step c), on a display device forming part of the fluid processing medical apparatus;
e) receiving a manual selection of one of the suitable therapies displayed on the display device, wherein step b) and step c) and step d) are performed automatically by a control system being connected with or forming part of the fluid processing medical apparatus; and
f) coupling the first disposable component with the fluid processing medical apparatus for performing said one of the suitable therapies, and
wherein, if the first disposable component is confirmed to be expired in step b), then the method proceeds with:
g) providing an acoustical or optical warning that informs a user that the first disposable component is expired;
h) instructing the user to position a second disposable component relative to the reader unit; and
i) reading component related information provided on the second disposable component by the reader unit, the component related information provided on the second disposable component including a second date of expiration.

2. The method according to claim 1, further comprising the step of:
i) manually returning, by the user, to one of step a) or step b) if the selection displayed in step e) does not meet expectations of the user.

3. The method according to claim 1, wherein step f) comprises manually selecting one of the suitable therapies on a touch screen.

4. The method according to claim 1, wherein the database comprises a concordance table or concordance matrix assigning the component related information to component related data based on at least one of a group of identity of the disposable component, identity of a series of identical disposable components, manufacturer, production details, production data, expiration date, therapies performable with the disposable component, or therapy data.

5. The method according to claim 1, further comprising the step of: changing the first disposable component after the therapy with an unused third disposable component, wherein at least steps a) to c) are performed again with the third disposable component.

6. A fluid processing medical apparatus, comprising:
a processor unit or control unit connected with or forming part of the fluid processing apparatus, the processor unit or control unit configured to control operation of the fluid processing medical apparatus;
a reader unit configured to automatically read component related information provided on a first disposable component to be used with the fluid processing medical apparatus and being positioned relative to the reader unit by a user, the component related information including a date of expiration; and
a display unit configured to display control and operation information of the fluid processing medical apparatus;

wherein the processor unit or control unit is configured to:
a) confirm that the first disposable component is unexpired based on the date of expiration;
b) automatically match component related information read by the reader unit with component related data if the first disposable component is confirmed to be unexpired, the component related data being stored in a database within the fluid processing medical apparatus or a database connected to the fluid processing medical apparatus via a network;
c) automatically provide a selection of suitable therapies for the first disposable component on the display unit to the user if the first disposable component is confirmed to be unexpired:
d) automatically provide an acoustical or optical warning to the user if the first disposable component is determined to be expired; and
e) instruct the user to read component related information provided on a second disposable component if the first disposable component is determined to be expired.

7. The fluid processing medical apparatus according to claim 6, wherein the display unit is a touch screen configured to allow a user to manually select a desired therapy from the selection of suitable therapies displayed on the display unit; and
the processor unit or control unit is configured to operate components of the fluid processing medical apparatus in accordance with the desired therapy.

8. The fluid processing medical apparatus according to claim 7, wherein the components include at least one of a peristaltic pump or a syringe.

9. The fluid processing medical apparatus according to claim 6, wherein the processor unit or control unit is configured to enable the user to read other component related information provided on a third disposable component by the reader unit in case the selection provided in step b) does not meet the requirements of the user.

10. The fluid processing medical apparatus according to claim 6, wherein the processor unit or control unit is configured to display on the display unit to the user one or more steps for correctly installing the first disposable component at the fluid processing medical apparatus after selection of a therapy if the first disposable component is confirmed to be unexpired.

11. The fluid processing medical apparatus according to claim 6, further comprising:
one or more sensors configured to detect a correct installation of the first disposable component if the first disposable component is determined to be unexpired, wherein the processor unit or control unit is configured to start the selected therapy only after correct installation of the first disposable component detected by the one or more sensors.

12. The fluid processing medical apparatus according to claim 6, wherein the database is within the fluid processing medical apparatus and comprises a concordance table or concordance matrix assigning the component related information to component related data based on at least one of group of identity of the first disposable component, identity of a series of identical disposable components, manufacturer, production details, production data, expiration date, therapies performable with the disposable component, or therapy data.

13. The fluid processing medical apparatus according to claim 12, wherein the component related information includes a disposable component-ID.

14. The fluid processing medical apparatus according to claim 6, wherein the processor unit or control unit is configured to deactivate the reader unit upon selection of the therapy type.

* * * * *